US00PP13734P29

(12) United States Plant Patent
Zwetzig et al.

(10) Patent No.: US PP13,734 P2
(45) Date of Patent: Apr. 22, 2003

(54) HIBISCUS PLANT NAMED 'ANGELIQUE'

(76) Inventors: Gretchen Angela Zwetzig, 8101 S. 14th St., Lincoln, NE (US) 68512; David Whitman Fleming, deceased, late of Lincoln, NE (US), by Gretchen Angela Zwetzig, legal representative ( * ) Notice: Subject to any disclaimer, the term of this patent is extended or adjusted under 35 U.S.C. 154(b) by 0 days.

(21) Appl. No.: 10/207,251

(22) Filed: Jul. 30, 2002

(51) Int. Cl.[7] ..... A01H 5/00
(52) U.S. Cl. ..... Plt./257
(58) Field of Search ..... Plt./257

*Primary Examiner*—Bruce R. Campell
*Assistant Examiner*—W C Haas

(57) ABSTRACT

A new and distinct cultivar of winter hardy hibiscus plant named 'Angelique' is the result of a unique hybridization. This new and distinct cultivar is characterized primarily as to novelty by its tropical aspects, its extreme cold hardiness to Zone 4, its medium-sized, thick-textured, tubular white flowers with red centers and recurved petal edges and its shiny "Maple-like" green leaves and unusual pyramidal compactness of about 3 feet, its vigorous and uniform growth habit, and its floriferous nature from midsummer until frost, and its genetic achievement as a cross between a tropical and hardy Hibiscus.

1 Drawing Sheet

BOTANICAL CLASSIFICATION

*Hibiscus moscheutos×H. rosa-sinensis.*

BACKGROUND OF THE NEW PLANT

The new plant of this invention is the result of a unique hybridization, with the breeding achievement being evidenced in the outstanding combination of characteristics exhibited by this new and distinct Hibiscus plant, which include:

(a) Refined and noticeably shiny, "Maple-like", green leaves which have smooth margins and white buds s which combined compliments the landscape;

(b) Medium-sized flowers that are outstanding for their bright white overlapping petals with red eyezones that have a tubular shape and recurved petal edges;

(c) The plant being very floriferous with flowers that stay open at least one full day, sometimes two;

(d) The plant being small but vigorous with stouter stems, compact and "pyramidal" breaking action which gives it unique landscape utility; and (e) The plant being so hardy that it can consistently withstand winter temperatures of a least −30 degrees Fahrenheit.

(f) The plant being a genetic achievement as a hybrid between a tropical and hardy Hibiscus.

SUMMARY OF THE INVENTION

'Angelique' was the result of a 40-year breeding program. Its ancestry includes *Hibiscus moscheutos* and *Hibiscus rosa-sinensis.* More specifically, the plant resulted from multiple crossings with an unnamed Fleming *Hibiscus rosa-sinensis* (nonpatented) and 'Bright Eye', a Fleming *Hibiscus moscheutos* (nonpatented). The seedling which most nearly met all of the above named standards was selected.

This new plant first bloomed in the summer of 1989 and was selected by David Fleming and Gretchen Zwetzig on David Fleming's property in Lincoln, Nebr. Asexual propagation of the plant by cuttings and root division has shown that unique and distinguishing features of the plant are faithfully transmitted from generation to generation and appear to be fixed.

Since its origin, the plant has bloomed from midsummer until frost, while exhibiting the aforementioned distinctive charateristics. This TROPICAL—HARDY™ Hibiscus plant greatly contributes to the market with its tropical aspect, sheer beauty and utter refinement, its compact growth habit, its enhanced resistance to disase and insects, its stability through extremes in rain and drought, and its extreme hardiness.

BRIEF DESCRIPTION OF THE DRAWINGS

The flower and foliage of the cultivar are shown in the attached photograph. More specifically, the photograph is a close-up of the flower and the leaf.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with the *Dictionary of Color* (Maerz and Paul), while general color recitations are consistent with ordinary American color terminology.

'Angelique' has not been observed under all possible environmental conditions. It is to be understood that the phenotype may vary significantly with variations in environment such as temperature, light intensity, and day length, without, however any difference in genotype of the plant. The following botanical characteristics and observations are gathered from the plant when grown in Lincoln, Nebr. (USDA Zone 4).

THE PLANT

Parentage:

*Seed parent.—Hibiscus moscheutos,* 'Bright Eye' an unpatented Fleming seedling.

*Pollen parent.*—*Hibiscus rosa-sinensis* Unnamed and unpatented Fleming seedling.

Origin: A selected seedling from stated cross.

Type of plant: Hardy, herbaceous perennial with some tropical genetics.

Classification: Variety of TROPICAL—HARDY™ Hibiscus plant.

Propagation: Relatively easy to propagate; holds its distinguishing characteristics through successive cuttings and division.

Size: About 3–3½ feet tall and about 2 ft. wide.

Form: Symmetrical annual growth from perennial roots.

Habit: Upright and uniformly branched.

Growth: Vigorous; small and very compact. Full grown (3 ft.) in 2 years.

Hardiness: Hardy to at least −30 degrees Fahrenheit.

General health: Plant is very disease resistant against rot, aphids, spider mites, scale, white fly, etc.; sturdy through excessive drought, rain, or wind.

Propagation: Relatively easy and fast rooting in approximately 2 weeks.

Foliage:

1. *Arrangement.*—Alternate.
2. *Shape.*—Juvenile: Variable, 3-lobed leaf. Rounded base shape. Mature: Refined, "maple-like", 3–5 lobed leaf with entire to extremely mildly serrate margins, and acute apices; rounded base.
3. *Size.*—Mature leaf (petiole base to apex): Length is about 5¼ inches or 13½ cm, width is about 5 inches or 13 cm.
4. *Color.*—Young leaves (upper side): L-3, PLATE 4, page 71. Mature leaves: (upper side): J-1, PLATE 24, page 71. Veins: K-1, PLATE 46, page 115. Coloration of the lower leaf surface: 4-L, PLATE 23, page 69.
5. *Surface texture.*—Medium to High sheen.
6. *Petiole length.*—About 1¾ inches or 4½ cm.
7. *Petiole color.*—Green to K-9, PLATE 5, page 33.

Stems: The stems are stout at the base, becoming more slender toward the apices; coloration is consistent with the petiole.

THE FLOWER

Blooming period: Profuse from July until frost.

Flower diameter: Medium to large; about 8½ inches (21 cm).

Borne: Singly in leaf axils, from midpoint of stems upward.

Bloom duration: Individual bloom lasts at least one full day, sometimes 2.

Form: Campanulate; petals are also very overlapping with a conical shape and recurved petal edges.

Bud:

1. *Length.*—About 2½ inches (or 6½ cm) on day before opening.
2. *Color.*—2-A, PLATE 9, page 41.
3. *Surface texture.*—Semi-glabrous.
4. *Duration.*—One to two weeks.

Corolla: Having 5 petals.

1. *Petal character and dimensions.*—Campanulate and very overlapping. Length is about 4½ inches or 11 cm. Width is about 3½ inches or 10 cm,
2. *Coloration.*—Bright white petals with red center. (a) Bright white petals: 1-B, p.25, PLATE 1 Coloration of lower petal surface: 1-B, pg. 25, PLATE 1 (b) Veination in petals: 1-D, pg. 21, PLATE 4 (c) Eye Zone: 6-K, pg. 25, PLATE 1.
3. *Texture.*—Smooth.
4. *Substance.*—Thick.
5. *Shape.*—Campanulate and very overlapping; tubular with recurved petal edges.

Reproductive organs:

1. *Staminal column.*—Stamen along basal two-thirds. Stamen length: About 1.10 inches (or 4.5 cm). Stamen color: A-1, pg. 25, PLATE 1. Pollen color: J-1, PLATE 10, page 43.
2. *Style.*—Terminates upper one-third of staminal column. Stigmatic lobe color: H-1, pg. 43, PLATE 10.

Calyx: Connate at the base; about 1½ inches (or 4.5 cm) in length. Color: Medium green.

Stipules: None.

Epicalyx: Whorl of bracts.

1. *Shape.*—10 to 12 slender, sword-shaped bractlets.
2. *Length.*—About 1¼ inches (or 3 cm).
3. *Color.*—6-L, PLATE 22, page 67.

Penduncle:

1. *Length.*—About 4 inches (or 6 cm).
2. *Strength.*—Stiff and sturdy.
3. *Color.*—Light to medium green.

GENERAL OBSERVATIONS

This plant, as a hybridized TROPICAL—HARDY™ Hibiscus, is valuable to the landscape market for its improvements in tropical aspect, unique bright white, tubular, overlapping flowers, shiny and very refined, "Maple-like" green foliage on a much more compact, "pyramidal" plant, its all-around vigor, good breaking action, and adaptation to extreme environments, including the ability to consistently survive winter temperatures of at least −30 degrees Fahrenheit.

It is claimed:

1. A new and distinct cultivar of Hibiscus plant, as herein shown and described.

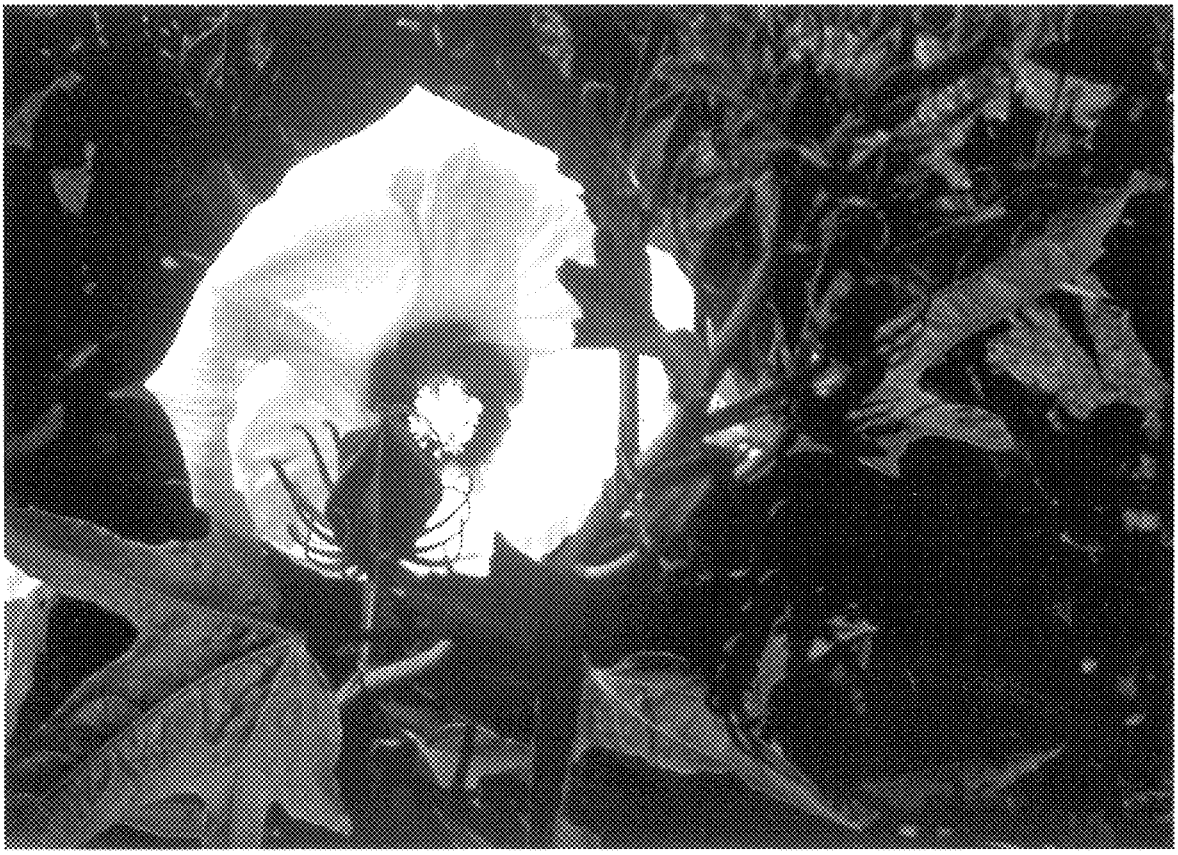

* * * * *